(12) United States Patent
Mire et al.

(10) Patent No.: US 10,463,401 B2
(45) Date of Patent: Nov. 5, 2019

(54) SPINAL IMPLANT SYSTEM AND METHODS OF USE

(71) Applicant: Warsaw Orthopedic, Inc, Warsaw, IN (US)

(72) Inventors: David A. Mire, Cordova, TN (US); Brian A. Butler, Atoka, TN (US); Molly K. Rice, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/658,635

(22) Filed: Jul. 25, 2017

(65) Prior Publication Data

US 2019/0029729 A1 Jan. 31, 2019

(51) Int. Cl.
*A61B 17/70* (2006.01)
*A61B 17/88* (2006.01)
*A61B 17/00* (2006.01)
*A61B 17/56* (2006.01)

(52) U.S. Cl.
CPC ...... *A61B 17/7032* (2013.01); *A61B 17/7002* (2013.01); *A61B 2017/00004* (2013.01); *A61B 2017/00862* (2013.01); *A61B 2017/00867* (2013.01); *A61B 2017/00893* (2013.01); *A61B 2017/00915* (2013.01); *A61B 2017/00933* (2013.01); *A61B 2017/00955* (2013.01); *A61B 2017/00964* (2013.01); *A61B 2017/564* (2013.01)

(58) Field of Classification Search
CPC ............ A61B 17/7032; A61B 17/7002; A61B 2017/00004; A61B 2017/00862; A61B 2017/00867; A61B 2017/00893; A61B 2017/00915; A61B 2017/00933; A61B 2017/00955; A61B 2017/00964; A61B 2017/564
USPC .......................................... 606/264–270, 279
See application file for complete search history.

(56) References Cited

U.S. PATENT DOCUMENTS

| | | | |
|---|---|---|---|
| 5,129,899 A * | 7/1992 | Small | A61B 17/7007 606/286 |
| 5,885,286 A | 3/1999 | Sherman et al. | |
| 6,565,566 B1 | 5/2003 | Wagner et al. | |
| 6,669,697 B1 * | 12/2003 | Pisharodi | A61B 17/7007 606/250 |
| 8,034,089 B2 | 10/2011 | Matthis et al. | |
| 8,097,025 B2 | 1/2012 | Hawkes et al. | |
| 8,167,910 B2 | 5/2012 | Nilsson | |
| 8,197,518 B2 | 6/2012 | Hammill, Sr. et al. | |
| 8,298,265 B2 | 10/2012 | Purcell et al. | |
| 8,298,275 B2 | 10/2012 | Rezach | |
| 10,085,773 B2 * | 10/2018 | Asaad | A61B 17/8605 |
| 2003/0093078 A1 * | 5/2003 | Ritland | A61B 17/7007 606/900 |
| 2005/0033295 A1 * | 2/2005 | Wisnewski | A61B 17/7011 606/250 |
| 2007/0270839 A1 | 11/2007 | Jeon et al. | |

(Continued)

*Primary Examiner* — Pedro Philogene
*Assistant Examiner* — David C Comstock

(57) ABSTRACT

A spinal construct adaptor comprising a member disposable between an inner surface of a bone fastener that defines an implant cavity and a spinal rod disposed with the implant cavity. A capture element is connected with the member and engageable with the spinal rod. Implants, spinal constructs, systems, instruments and methods are disclosed.

20 Claims, 14 Drawing Sheets

(56) References Cited

U.S. PATENT DOCUMENTS

2010/0298891 A1* 11/2010 Jackson ............. A61B 17/7008
                                                        606/308
2011/0093021 A1    4/2011 Fanger et al.
2013/0190823 A1*  7/2013 Thompson ........... A61B 17/702
                                                        606/265

* cited by examiner

SPINAL IMPLANT SYSTEM AND METHODS OF USE

TECHNICAL FIELD

The present disclosure generally relates to medical devices for the treatment of spinal disorders, and more particularly to a surgical implant system including a bone fastener and a related method.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal construct adaptor is provided. The spinal construct adaptor comprises a member disposable between an inner surface of a bone fastener that defines an implant cavity and a spinal rod disposed with the implant cavity. A capture element is connected with the member and engageable with the spinal rod. In some embodiments, implants, spinal constructs, systems, instruments and methods are disclosed.

In one embodiment, a method of treating a spine is provided. The method comprising the steps of: reducing a spinal rod with an implant cavity of a bone fastener, the bone fastener including an inner surface defining the implant cavity; connecting an adaptor to the spinal rod; and positioning the adaptor between the inner surface and the spinal rod to selectively dispose the spinal rod relative to the inner surface to facilitate reduction of the spinal rod with the implant cavity.

In one embodiment, a spinal implant system is provided. The spinal implant system comprises a bone fastener including an implant receiver having a crown. A spinal rod is disposable within the implant receiver. An adaptor is positionable between the crown and the spinal rod to selectively dispose the spinal rod relative to the crown.

BRIEF DESCRIPTION OF THE DRAWINGS

The present disclosure will become more readily apparent from the specific description accompanied by the following drawings, in which.

DETAILED DESCRIPTION

Figure 1:
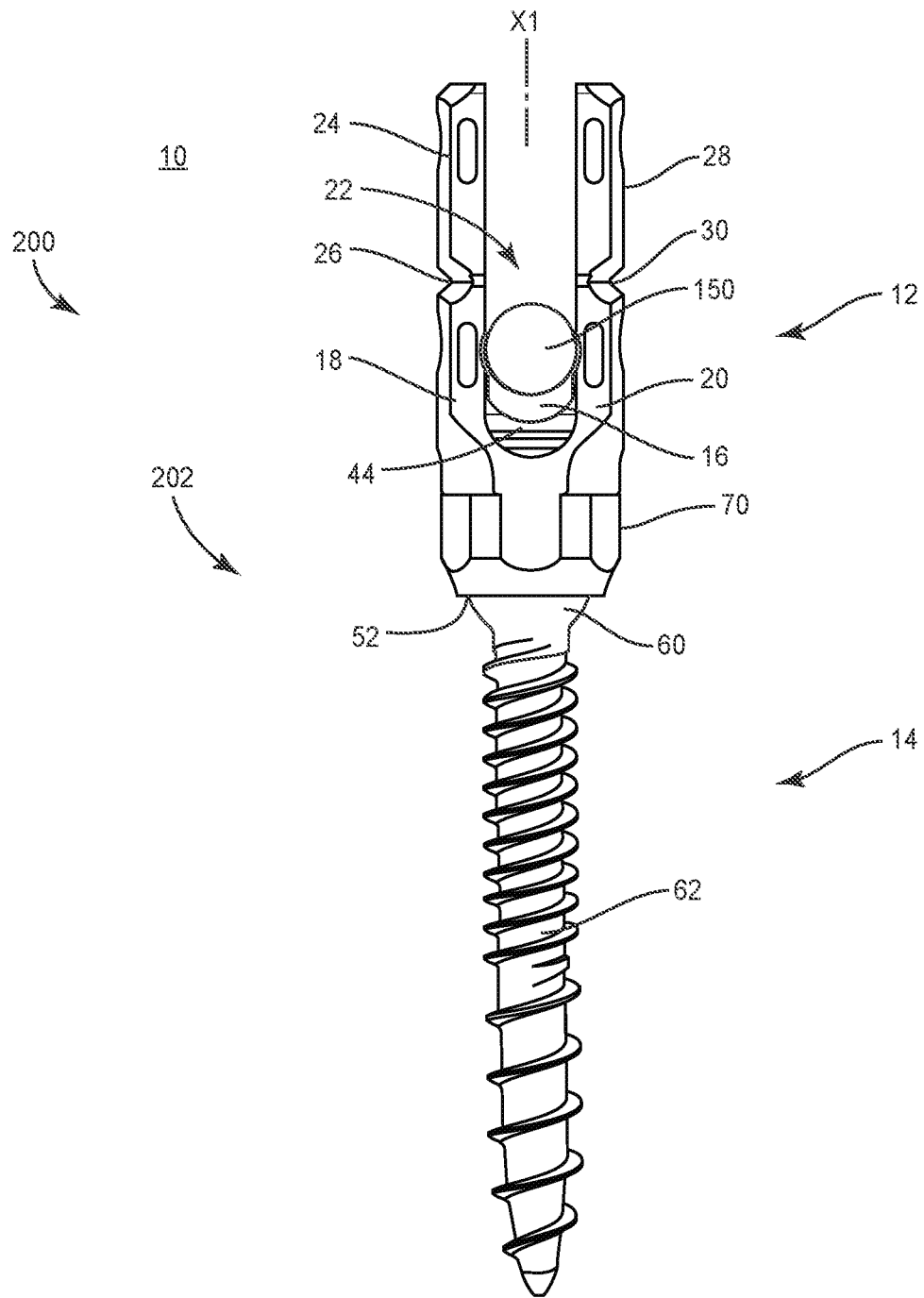
FIG. 1 is a side view of components of one embodiment of a spinal implant system in accordance with the principles of the present disclosure.
Figure 2:
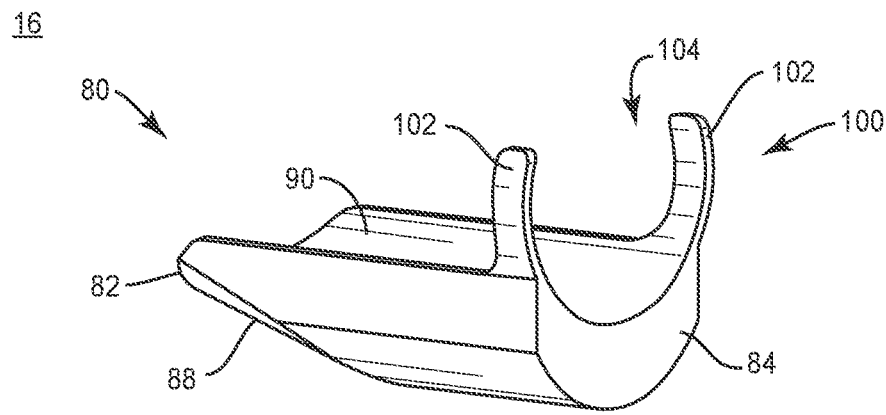
FIG. 2 is a perspective view of components of the system shown in FIG. 1.
Figure 3:
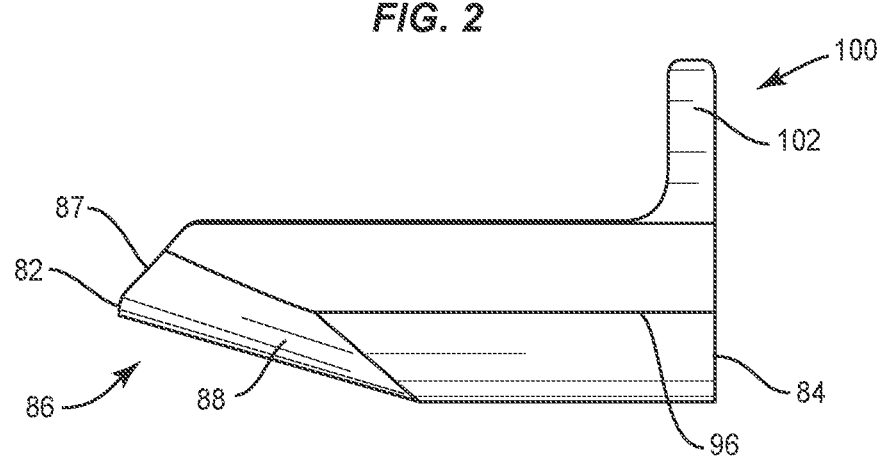
FIG. 3 is a side view of components of the system shown in FIG. 1.

The exemplary embodiments of a surgical system and related methods of use disclosed are discussed in terms of medical devices for the treatment of musculoskeletal disorders and more particularly, in terms of a spinal implant system including a bone fastener. In some embodiments, the present spinal implant system includes an implant comprising a bone fastener, such as, for example, a pedicle bone screw, an adaptor and a spinal rod for reduction with the bone screw. In some embodiments, the spinal rod reduction height is adjustable.

In some embodiments, the present spinal implant system comprises an adjustable height spinal rod. In some embodiments, the spinal implant system comprises a spinal construct including intra-operative spinal rod height adjustment. In some embodiments, the spinal implant system is employed with a method of treating a spinal deformity with correction surgery. In some embodiments, the spinal construct provides spinal rod height adjustment such that a reduction can be stopped and/or interrupted intra-operatively. In some embodiments, the reduction can be stopped and/or interrupted intra-operatively prior to a spinal rod being completely reduced into a head of a bone screw, for example, to avoid, resist and/or prevent bone/screw purchase being comprised. In some embodiments, the spinal construct provides spinal rod height adjustment such that the reduction can be stopped and/or interrupted to ensure that the spinal construct will maintain integrity with tissue.

In some embodiments, the spinal construct provides spinal rod height adjustment such that reduction can be stopped and/or interrupted at different heights with a spinal construct adaptor, such as, for example, a shim. In some embodiments, the shim can include multiple shapes and heights and is attachable to a spinal rod. In some embodiments, the shim can slide along a spinal rod to a position where the spinal rod is seated in a screw head. In some embodiments, the shim provides spinal rod height adjustment such that a reduction can be stopped and/or interrupted intra-operatively. In some embodiments, the shim can stop and/or interrupt reduction at various heights, for example, to compensate for a patient anatomy or in connection with a procedure.

In some embodiments, the spinal implant system comprises a spinal construct including intra-operative spinal rod height adjustment, which may be employed with a larger dorsal screw head. In some embodiments, the spinal implant system comprises a spinal construct including intra-operative spinal rod height adjustment, which provides intra-operative flexibility to customize the spinal construct configuration, as described herein.

In some embodiments, the spinal implant system comprises a spinal construct including an attachable shim, which provides intra-operative spinal rod height adjustment. In some embodiments, the shim allows for adjustment of a relative height of a spinal rod to a crown within a head of a bone screw. In some embodiments, the shim is attached to the spinal rod and slid along the spinal rod to a gap in the head of the bone screw between the spinal rod and the crown. The shim is disposed with the gap. In some embodiments, the configuration of the shim resists and/or prevents bone/screw purchase being comprised, for example, to avoid the risks of bone screw pull out from tissue, for example, associated with attempting complete reduction of a spinal rod with a head of a bone screw. In some embodiments, the shim includes a straight configuration. In some embodiments, the shim includes a tapered configuration. In some embodiments, the shim includes a wedge configuration disposable between a spinal rod and a crown of a bone screw head.

In some embodiments, the shim includes a bottom mating surface that includes a similar configuration to that of an outer surface of a spinal rod such that the mating surface engages the shape of the spinal rod. In some embodiments, the shim includes a mating surface that engages the spinal rod in an easy fit, snap fit and/or pop-on fit. In some embodiments, the shim allows for disposal with the spinal rod and the bone screw to account for bone quality and/or spinal rod curvature after the rod is positioned with the spinal construct. In some embodiments, the shim snaps onto the spinal rod and slides down the spinal rod to adjacent the bone screw, such as a reduction multi-axial bone screw or a multi-axial bone screw with additional dorsal height.

In some embodiments, the shim includes a tapered tip. In some embodiments, the shim includes a straight tip. In some embodiments, the spinal implant system is employed with a method of treating a spine including the steps of positioning a spinal construct adaptor with a spinal rod. In some embodiments, the method includes the steps of positioning the shim with a top surface of the spinal rod, relative to a bone screw, engaging the shim with the spinal rod in a snap fit, rotating the shim about the spinal rod, positioning the shim with a bottom surface of the spinal rod, and sliding the shim along the spinal rod into a cavity disposed between a portion of the spinal rod disposed with the bone screw and a crown of the bone screw.

In some embodiments, the spinal implant system provides the flexibility to make adjustment to a spinal construct during a surgical procedure. In some embodiments, the spinal implant system allows spinal construct adjustment while avoiding the need for rod bending, loss of bone-screw interface strength and/or bone screw pull out. In some embodiments, the spinal implant system allows spinal construct adjustment to screw height to accommodate rod position relative to vertebrae. In some embodiments, the spinal implant system comprises components of a spinal construct that may be connected together during manufacturing or intra-operatively, such as, for example, during a surgical procedure in an operating room. In some embodiments, the spinal construct adaptor is configured for assembly to a spinal construct without the use of an instrument, such as, for example, by a practitioner, surgeon and/or medical staff utilizing their hands for assembly.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a spinal construct and an adaptor, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-6, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal construct 200 having one or more spinal implants, such as, for example, a bone fastener 202 and an adaptor 16. Adaptor 16 is positioned with an implant receiver 12 of bone fastener 202 to selectively dispose a spinal rod 150 relative to bone fastener 202 and/or tissue, as described herein. In some embodiments, bone fastener 202 and adaptor 16 are assembled in situ and/or intra-operatively to form spinal construct 200, as described herein. Spinal construct 200 provides intra-operative spinal rod reduction height adjustment. In some embodiments, spinal construct 200 provides spinal rod height adjustment such that a reduction can be stopped and/or interrupted intra-operatively, and adaptor 16 disposed between spinal rod 150 and bone faster 202 for reduction height adjustment, as described herein. In some embodiments, reduction of spinal rod 150 with bone fastener 202 can be stopped and/or interrupted intra-operatively prior to spinal rod 150 being completely reduced with bone fastener 202 to avoid, resist and/or prevent bone/screw purchase being comprised, and to maintain integrity with tissue.

Bone fastener 202 includes an implant receiver 12 and a screw shaft 14, as shown in FIG. 1. Implant receiver 12 extends along and defines an axis X1. Implant receiver 12 includes a pair of spaced apart arms 18, 20 that define an implant cavity 22 therebetween configured for disposal of one or more components of spinal construct 200. Arms 18, 20 each extend parallel to axis X1. In some embodiments, arm 18 and/or arm 20 may be disposed at alternate orientations, relative to axis X1, such as, for example, transverse, perpendicular and/or other angular orientations such as acute or obtuse, coaxial and/or may be offset or staggered. Arms 18, 20 each include an arcuate outer surface extending between a pair of side surfaces. At least one of the outer surfaces and the side surfaces of arms 18, 20 have at least one recess or cavity therein configured to receive an insertion tool, compression instrument and/or instruments for inserting and tensioning bone fastener 202.

Arm 18 includes a break away tab 24 that is frangibly connected to arm 18 at a portion 26. In some embodiments, portion 26 is fabricated from a fracturing and/or frangible material such that manipulation of tab 24 relative to arm 18 can fracture and separate tab 24 from arm 18 along portion 26 at a predetermined force and/or torque limit, as described herein. In some embodiments, as force and/or torque is applied to tab 24 and resistance increases, for example, the predetermined torque and force limit is approached. Arm 20 includes a break away tab 28 that is frangibly connected to arm 20 at a portion 30. In some embodiments, portion 30 is fabricated from a fracturing and/or frangible material such that manipulation of tab 28 relative to arm 20 can fracture and separate tab 28 from arm 20 along portion 30 at a predetermined force and/or torque limit, as described herein. In some embodiments, as force and/or torque is applied to tab 28 and resistance increases, for example, the predetermined torque and force limit is approached.

In some embodiments, tabs 24, 28 can fracture and separate at a predetermined force or torque limit, which may be in a range of approximately 2 Newton meters (N-m) to 8 Nm. In some embodiments, tabs 24, 28 and arms 18, 20 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of tabs 24, 28 from arms 18, 20.

Cavity 22 is substantially U-shaped. In some embodiments, all or only a portion of cavity 22 may have alternate cross section configurations, such as, for example, closed, V-shaped, W-shaped, oval, oblong triangular, square, polygonal, irregular, uniform, non-uniform, offset, staggered, and/or tapered. Implant receiver 12 includes thread forms configured for engagement with a coupling member, such as, for example, a setscrew 36 (FIG. 9) to retain spinal rod 150 within cavity 22. In some embodiments, the inner surface of implant receiver 12 may be disposed with the coupling member in alternate fixation configurations, such as, for example, friction fit, pressure fit, locking protrusion/recess, locking keyway and/or adhesive. In some embodiments, all or only a portion of the inner surface of implant receiver 12 may have alternate surface configurations to enhance engagement with spinal rod 150 and/or setscrew 36, such as, for example, rough, arcuate, undulating, mesh, porous, semi-porous, dimpled and/or textured. In some embodiments, implant receiver 12 may include alternate configurations, such as, for example, closed, open and/or side access. Bone fastener 202 includes a crown 44 configured to facilitate positioning of spinal rod 150.

Implant receiver 12 defines a cavity 52 configured for disposal of a head 60 of screw shaft 14, as described herein. Head 60 includes a tool engaging portion configured to engage a surgical tool or instrument, as described herein. Screw shaft 14 includes a shaft 62 configured to penetrate tissue, such as, for example, bone and includes an outer surface having an external thread form. In some embodiments, the external thread form may include a single thread turn or a plurality of discrete threads.

In some embodiments, implant receiver 12 is manually engageable with head 60 in a non-instrumented assembly, as described herein. In some embodiments, manual engagement and/or non-instrumented assembly of implant receiver 12 and head 60 includes coupling without use of separate and/or independent instrumentation engaged with the components to effect assembly. In some embodiments, manual engagement and/or non-instrumented assembly includes a practitioner, surgeon and/or medical staff grasping implant receiver 12 and screw shaft 14 and forcibly assembling the components. In some embodiments, manual engagement and/or non-instrumented assembly includes a practitioner, surgeon and/or medical staff grasping implant receiver 12 and screw shaft 14 and forcibly snap fitting the components together, as described herein. In some embodiments, manual engagement and/or non-instrumented assembly includes a practitioner, surgeon and/or medical staff grasping implant receiver 12 and screw shaft 14 and forcibly pop fitting the components together and/or pop fitting implant receiver 12 onto screw shaft 14, as described herein. In some embodiments, a force in a range of 2-50 N is required to manually engage implant receiver 12 and screw shaft 14 and forcibly assemble the components. In some embodiments, a force in a range of 5-10 N is required to manually engage implant receiver 12 and screw shaft 14 and forcibly assemble the components.

In some embodiments, implant receiver 12 is connectable with screw shaft 14 to include various configurations, such as, for example, a posted screw, a pedicle screw, a bolt, a bone screw for a lateral plate, an interbody screw, a uni-axial screw (UAS), a fixed angle screw (FAS), a multi-axial screw (MAS), a side loading screw, a sagittal adjusting screw (SAS), a transverse sagittal adjusting screw (TSAS), an awl tip (ATS), a dual rod multi-axial screw (DRMAS), midline lumbar fusion screw and/or a sacral bone screw.

Adaptor 16 includes a member, such as, for example, a shim 80. Shim 80 is configured as a wedge for disposal with a space S (FIG. 9) between spinal rod 150 and an inner surface of implant receiver 12 during reduction. Shim 80 is configured for disposal with implant receiver 12 to selectively dispose spinal rod 150 relative to a surface of implant cavity 22, for example, crown 44. In some embodiments, shim 80 is configured for disposal between crown 44 and spinal rod 150 to selectively dispose spinal rod 150 relative to crown 44. In some embodiments, shim 80 is configured for disposal with implant receiver 12 to selectively adjust a dorsal height of spinal rod 150 relative to tissue connected with bone fastener 202. In some embodiments, adaptor 16 provides intra-operative spinal rod height adjustment, which provides intra-operative flexibility to customize the configuration of spinal construct 200, as described herein. In some embodiments, adaptor 16 provides intra-operative spinal rod height adjustment while avoiding the need for rod bending, loss of bone-screw interface strength and/or bone screw pull out. In some embodiments, adaptor 16 provides intra-operative spinal rod height adjustment to allow spinal construct adjustment to screw height to accommodate rod position relative to vertebrae.

Figure 9:
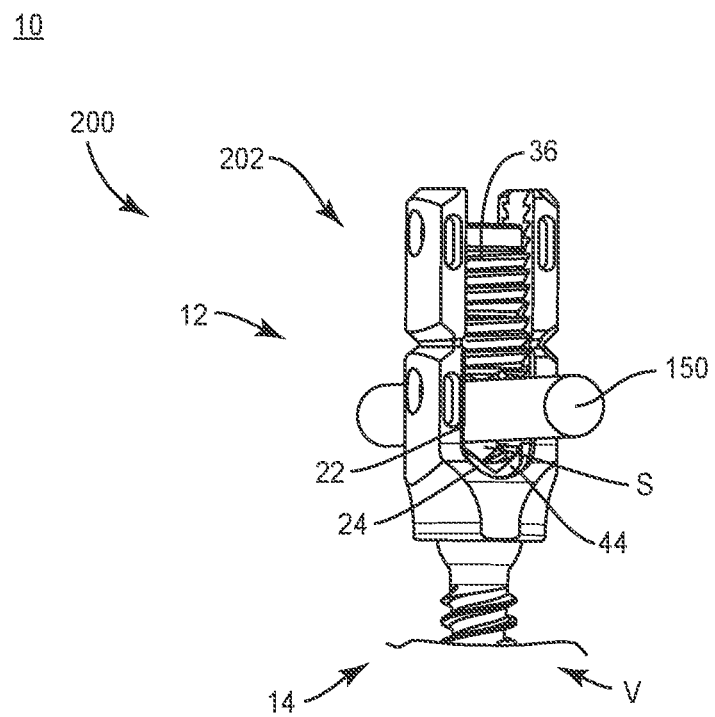
FIG. 9 is a perspective view of components of one embodiment of a spinal implant system in accordance with the principles of the present disclosure disposed with vertebrae.

Shim 80 extends between an end 82 and an end 84. Shim 80 includes a surface 86 disposed between ends 82, 84. End 82 includes a tip 86 having a bevel end surface 87. Tip 86 includes a tapered surface 88. Surfaces 87, 88 comprise a wedge configuration to facilitate engagement of tip 86 with spinal rod 150 and crown 44, and disposal of shim 80 with space S. The thickness of shim 80 provides selective adjustment of the distance of spinal rod 150 relative to crown 44. A variation in a thickness of surface 88 facilitates selectively adjusting the distance of spinal rod 150 relative to crown 44 by allowing shim 80 to be translated along surface 88 providing for varied depths of tip 86 for optimal fit within space S (FIG. 9). For example, as surface 88 translates relative to spinal rod 150, shim 80 provides a wedge to fill space S between spinal rod 150 and crown 44.

Shim 80 includes an arcuate surface 90 that is slidably engageable with an outer arcuate surface of spinal rod 150. As shim 80 is engaged with bone fastener 202, surface 90 translates and/or rotates along a surface of spinal rod 150 to facilitate insertion and/or positioning of shim 80 relative to crown 44 and spinal rod 150. In some embodiments, all or only a portion of surface 90 may have alternate surface configurations, such as, for example, rough, arcuate, undulating, mesh, porous, semi-porous, dimpled and/or texture.

Figure 4:
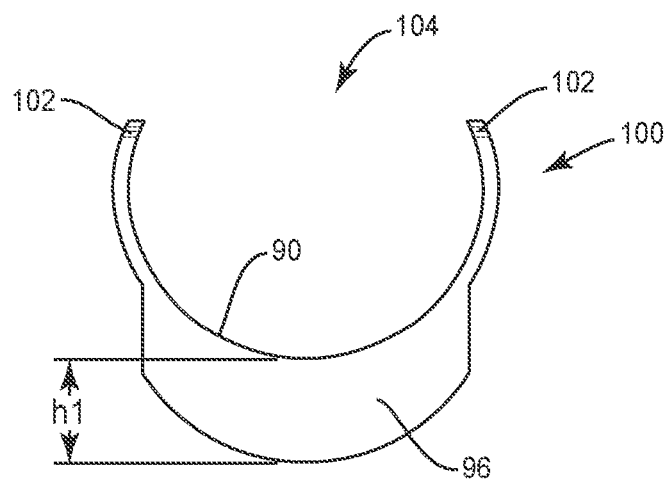
FIG. 4 is an end view of the components shown in FIG. 1.
Figure 5:
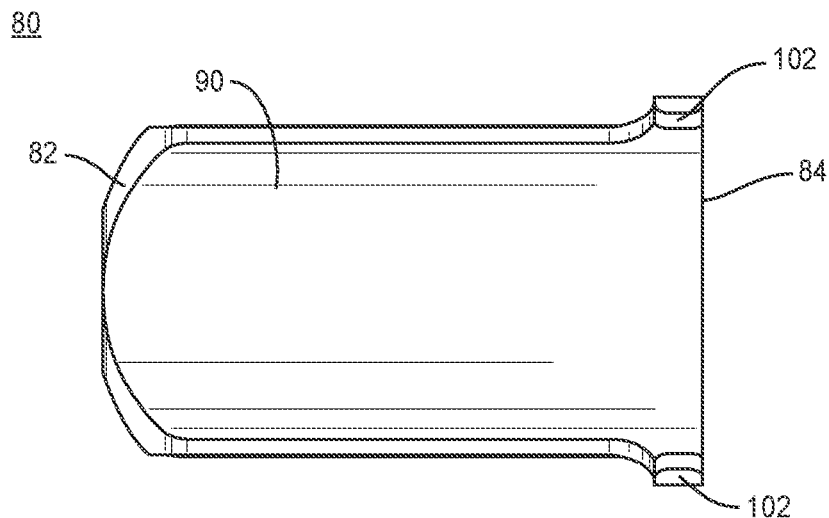
FIG. 5 is a side view of the components shown in FIG. 1.
Figure 6:
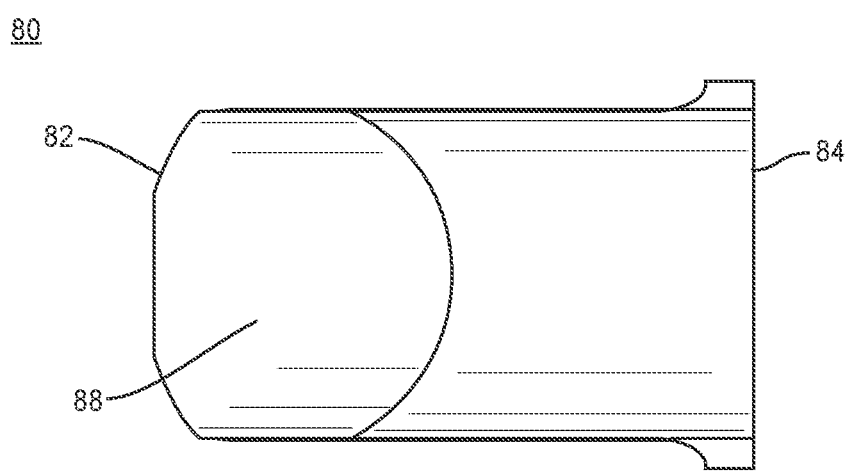
FIG. 6 is a side view of the components shown in FIG. 1.
Figure 7:
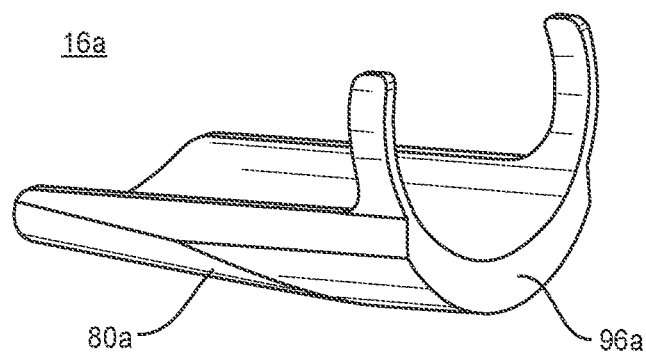
FIG. 7 is a perspective view of components of one embodiment of a spinal implant system in accordance with the principles of the present disclosure.
Figure 8:
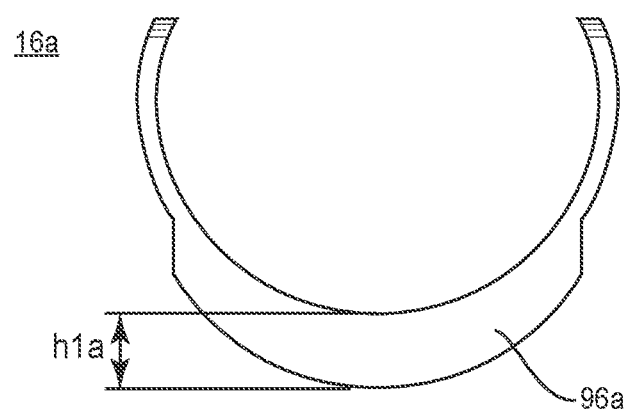
FIG. 8 is an end view of the components shown in FIG. 7.

End 84 includes a portion 96 having a height h1, as shown in FIG. 4. Portion 96 is disposable between spinal rod 150 and crown 44 to facilitate reduction of spinal rod 150 at a selected height, as described herein. In some embodiments, spinal implant system 10 comprises a spinal implant kit, as described herein, which includes a plurality of shims 80 having various sized portions 96, such as, for example, adaptor 16a including shim 80a having a portion 96a with a height h1a, as shown in FIGS. 7 and 8.

Adaptor 16 includes a capture element, such as, for example, a circumferential band 100 that extends to form end 84. Band 100 includes arms 102 that are moveable relative to shim 80. Arms 102 define an opening, such as, for example, a gap 104 therebetween, which facilitates expansion and contraction to capture spinal rod 150. For example, spinal rod 150 is oriented into alignment with gap 104. As arms 102 engage the surface of spinal rod 150, arms 102 expand to facilitate insertion of spinal rod 150 between arms 102. Upon insertion of spinal rod 150, arms 102 contract about spinal rod 150 in a snap-fit configuration. In the contracted orientation, arms 102 form a friction fit with the surface of spinal rod 150 to capture spinal rod 150. In some embodiments, the capture element includes an expandable ring.

In assembly, operation and use, spinal implant system 10, similar to the systems and methods described herein, is employed with a surgical procedure for treating disorders of the spine, such as those described herein, as shown in FIGS. 9-13. In some embodiments, one or all of the components of spinal implant system 10 can be delivered as a pre-assembled device or can be assembled in situ.

A surgical treatment including spinal implant system 10 can be used for correction and alignment in stabilization of a treated section of vertebrae. In an exemplary use, a medical practitioner obtains access to a surgical site via a posterior surgical approach. In some embodiments, the surgical site may be accessed in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae is accessed through a mini-incision, or sleeve that provides a protected passageway to the area.

An incision is made in the body of a patient and a cutting instrument (not shown) creates a surgical pathway for delivery and implantation of components of spinal implant system 10 with vertebrae. A preparation instrument (not shown) can be employed to prepare tissue surfaces of vertebrae, as well as for aspiration and irrigation of a surgical region.

Spinal implant system 10 includes spinal construct 200 having bone fasteners 202, as described herein, which are delivered to the surgical site for disposal with vertebrae V in connection with the surgical procedure. In some embodiments, one or more bone fasteners 202 are disposed in a serial and/or substantially linear orientation along vertebrae. In some embodiments, one or more bone fasteners 202 are disposed with vertebrae V in alternate orientations relative to each other, such as, for example, parallel, perpendicular, adjacent, co-axial, co-planar, arcuate, offset, staggered, transverse, angular and/or relative posterior/anterior orientations and/or at alternate vertebral levels.

Pilot holes are made in a selected orientation. Bone fasteners 202 are aligned with the pilot holes and fastened with the tissue of vertebrae V. Implant receiver 12 is engaged with screw shaft 14, as described herein. In some embodiments, the components of bone fastener 202 can be pre-operatively or intra-operatively connected and/or assembled. In some embodiments, screw shaft 14 can be connected with tissue and implant receiver 12 intra-operatively connected and/or assembled therewith. In some embodiments, bone fastener 202 is assembled in a non-instrumented assembly on a back table of an operating room during a surgical procedure, as described herein. In some embodiments, bone fastener 202 is assembled in an instrumented assembly.

Spinal construct 200 includes spinal rod 150, as described herein, which is shaped, contoured and/or bent to a selected configuration for a selected curvature or final lordosis of vertebrae V, as attached with bone fasteners 202 in connection with the surgical procedure. Spinal rod 150 is delivered to the surgical site and oriented for alignment with implant cavities 22 of bone fasteners 202. Reduction instruments are connected with bone fasteners 202 to reduce spinal rod 150 with implant cavities 22.

The reduction instruments manipulate each of bone fasteners 202. For example, spinal rod 150 is disposable with implant cavities 22 for reduction with implant receivers 12, however, spinal rod 150 may not fully seat within one or more implant cavities 22, as shown in FIG. 9, due to the selected shape, contour and/or bend of spinal rod 150. Spinal rod 150 is spaced apart a space S with crown 44.

Figure 10:
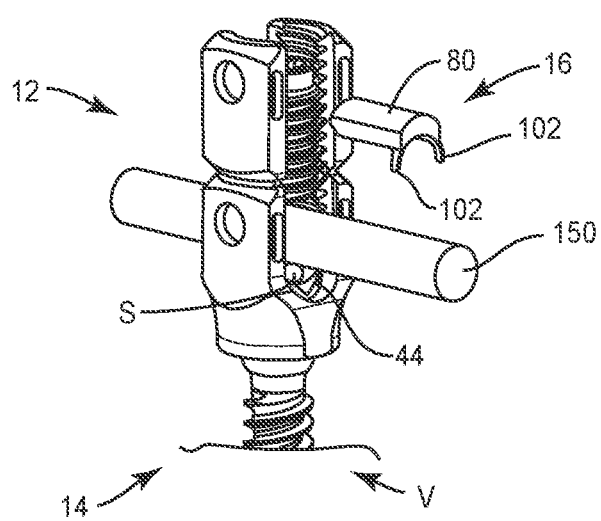
FIG. 10 is a perspective view of components of one embodiment of a spinal implant system in accordance with the principles of the present disclosure disposed with vertebrae.

Adapter 16 is delivered to the surgical site and oriented for alignment with a selected bone fastener 202 and spinal rod 150, as shown in FIG. 10 and described herein. Shim 80 is positioned to intra-operatively dispose spinal rod 150 relative to vertebrae V, accommodate rod position relative to vertebrae V, selectively dispose spinal rod 150 relative to crown 44 and/or adjust a dorsal height of spinal rod 150 relative to vertebrae V. Adaptor 16 provides intra-operative spinal rod height adjustment, which provides intra-operative flexibility to customize the configuration of spinal construct 200. In some embodiments, adaptor 16 provides intra-operative spinal rod height adjustment while avoiding the need for rod bending, loss of bone-screw interface strength and/or bone screw pull out.

Figure 11:
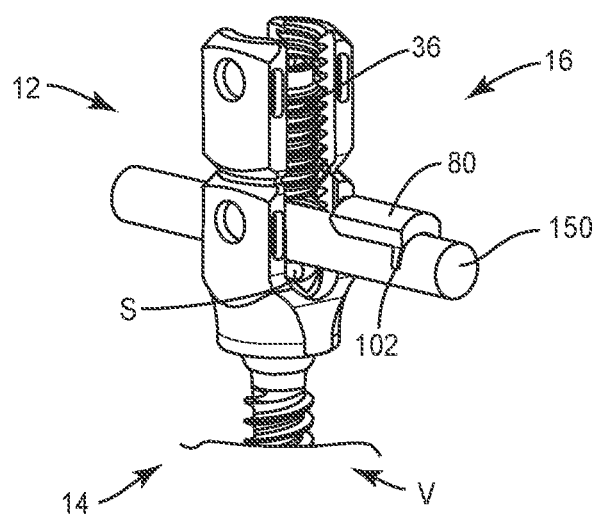
FIG. 11 is a perspective view of the components and vertebrae shown in FIG. 10.
Figure 12:
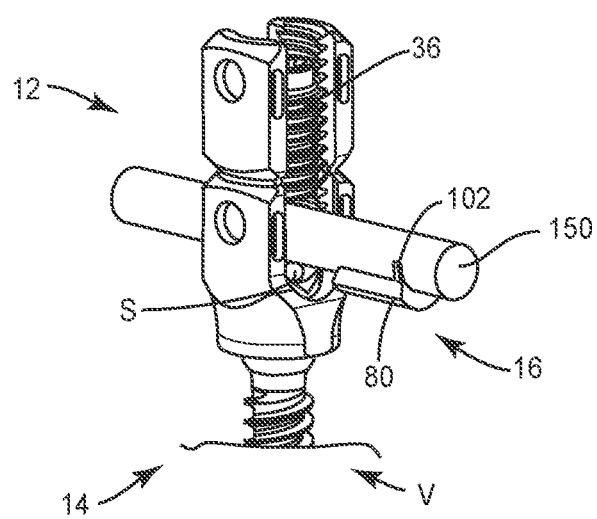
FIG. 12 is a perspective view of the components and vertebrae shown in FIG. 10.
Figure 13:
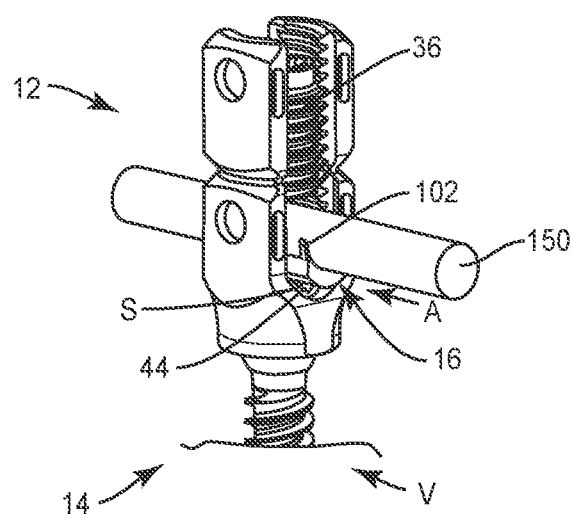
FIG. 13 is a perspective view of the components and vertebrae shown in FIG. 10.
Figure 14:
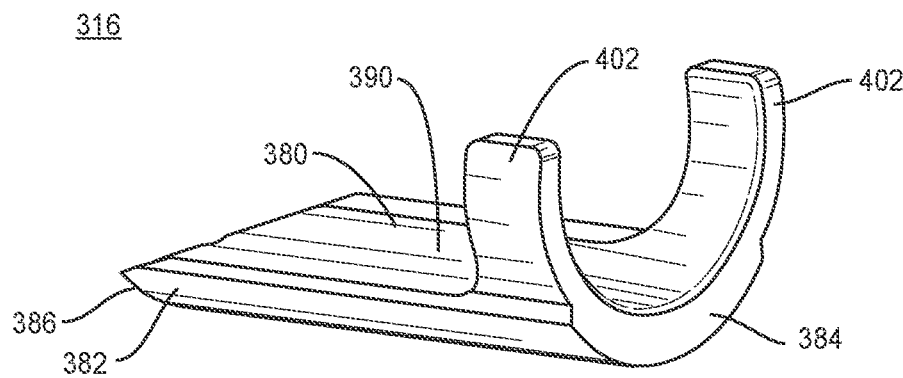
FIG. 14 is a perspective view of components of one embodiment of a spinal implant system in accordance with the principles of the present disclosure.
Figure 15:
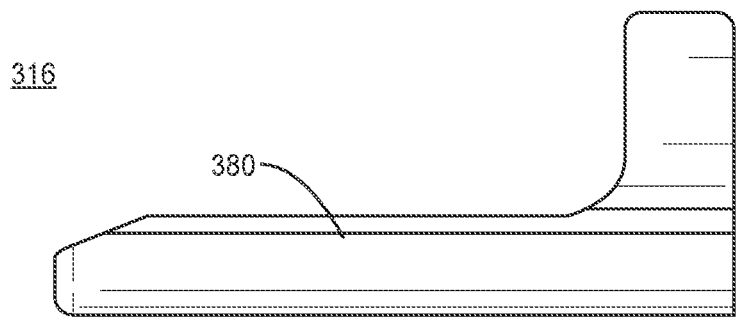
FIG. 15 is a side view of the components shown in FIG. 14.

Adaptor 16 is selected from a kit of a plurality of adaptors having various sized portions 96, as described herein. Adaptor 16 is aligned with a top surface of spinal rod 150, as shown in FIG. 10. Adaptor 16 is aligned such that gap 104 between arms 102 is disposed facing spinal rod 150. As adaptor 16 is translated into engagement with spinal rod 150, arms 102 engage the surface of spinal rod 150, and arms 102 expand to facilitate insertion of spinal rod 150 therebetween. Upon connection of spinal rod 150 with adaptor 16, arms 102 contract about spinal rod 150 in a snap-fit assembly, as shown in FIG. 11. Adaptor 16 is rotated about spinal rod 150, as shown in FIG. 12. Shim 80 is positioned in alignment with space S between spinal rod 150 and surface 24. Adaptor 16 is translated, in a direction shown by arrow A in FIG. 13, for insertion into space S between spinal rod 150 and crown 44. Shim 80 fills space S between spinal rod 150 and the surface of crown 44 to facilitate reduction height adjustment of spinal rod 150 relative to bone fastener 202 and/or the tissue of vertebrae V, as described herein.

Shim 80 is disposed with space S to seat spinal rod 150 with crown 44, and connect spinal construct 200 with vertebrae V. Set screws 36 are engaged with bone fasteners 202 to finally tighten spinal rod 150 for fixation with vertebrae V. In some embodiments, torque is applied to respective break off tabs for removal, as described herein.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

Upon completion of the procedure, the non-implanted components, surgical instruments and assemblies of spinal implant system 10 are removed and the incision is closed. In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In one embodiment, as shown in FIGS. 14-18, spinal implant system 10, similar to the systems and methods described herein, includes an adaptor 316, similar to adaptor 16 described herein. Adaptor 316 is disposable with implant receiver 12 of bone fastener 202, described herein, between spinal rod 150 and crown 44 to provide intra-operative spinal rod reduction height adjustment, as described herein.

Adaptor 316 includes a shim 380, similar to shim 80 described herein. Shim 380 extends linearly between an end 382 and an end 384. End 382 includes a tip 386 having a bevel end surface. Tip 386 comprises a wedge configuration to facilitate engagement of tip 386 with spinal rod 150 and crown 44, and disposal of shim 380 with space S. The thickness of shim 380 provides selective adjustment of the distance of spinal rod 150 relative to crown 44. Tip 386 is configured to adjust the distance of spinal rod 150 relative to crown 44. As tip 386 translates relative to spinal rod 150, shim 380 provides a wedge to fill space S between spinal rod 150 and crown 44.

Figure 16:
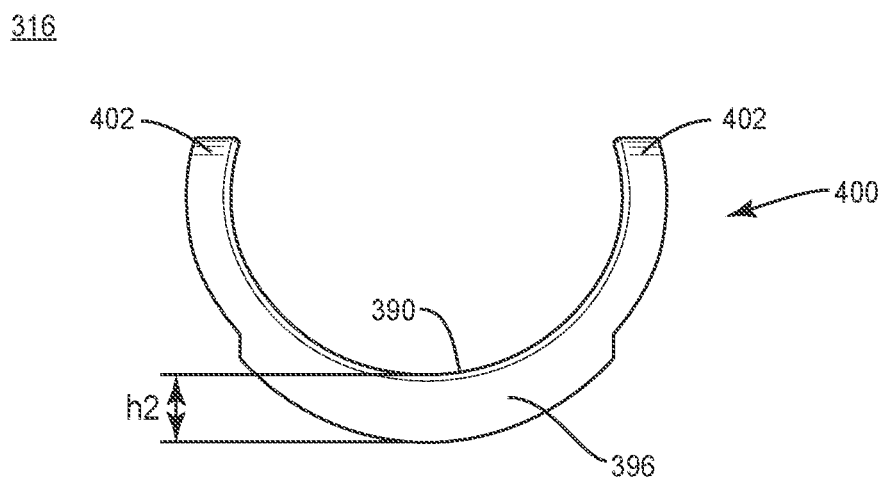
FIG. 16 is an end view of the components shown in FIG. 14.
Figure 17:
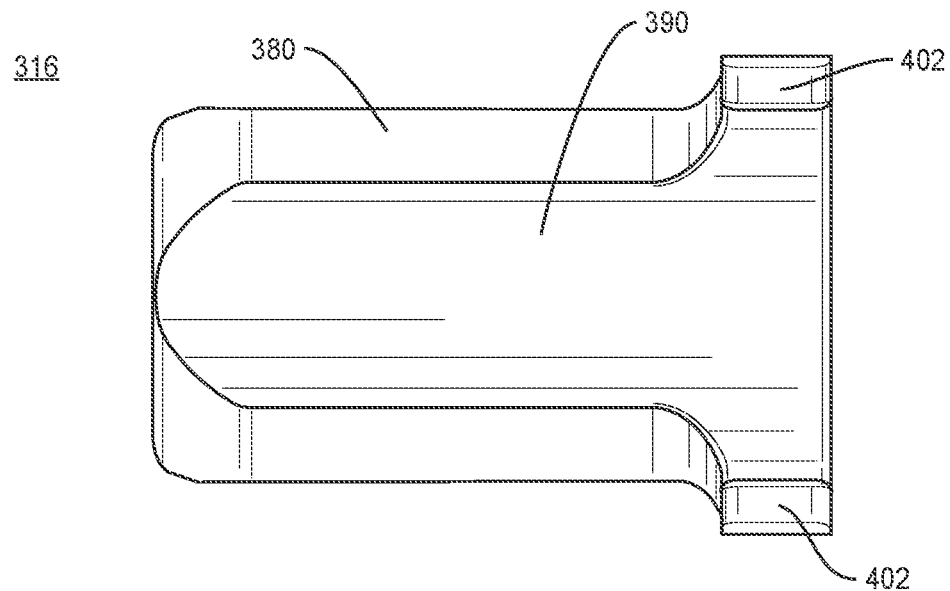
FIG. 17 is a side view of the components shown in FIG. 14.
Figure 18:
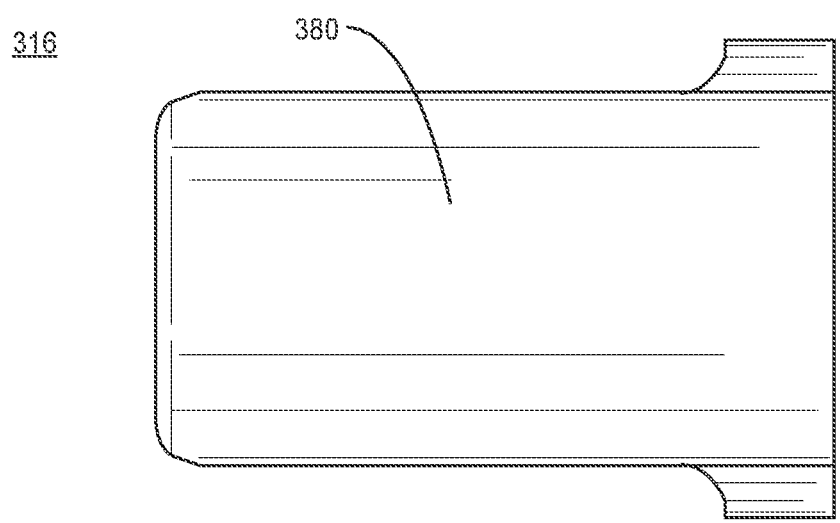
FIG. 18 is a side view of the components shown in FIG. 14.
Figure 19:
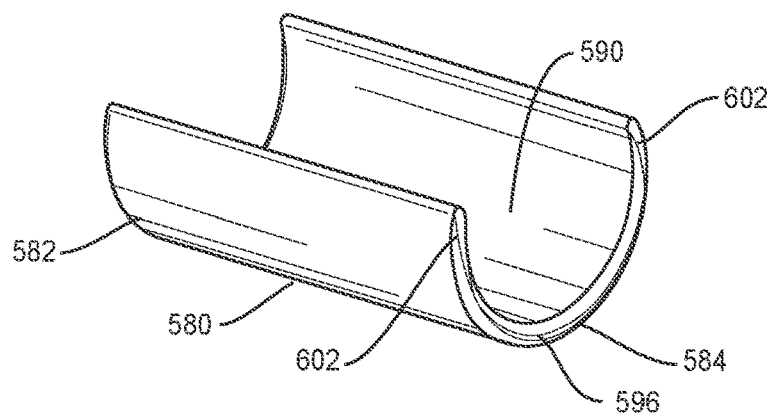
FIG. 19 is a perspective view of components of one embodiment of a spinal implant system in accordance with the principles of the present disclosure.
Figure 20:
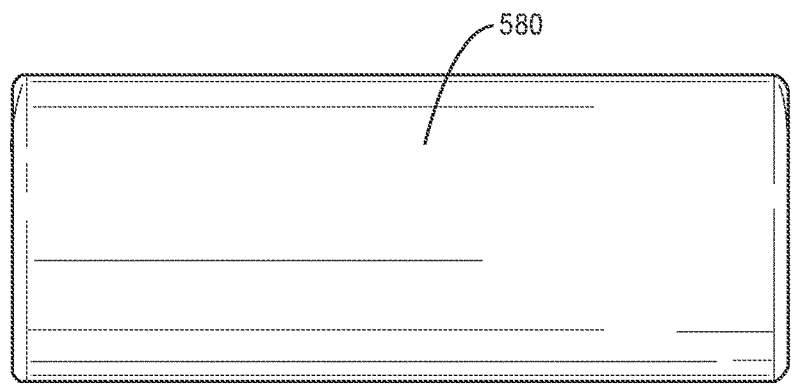
FIG. 20 is a side view of the components shown in FIG. 19.

Shim 380 includes an arcuate surface 390 that is slidably engageable with an outer arcuate surface of spinal rod 150, as described herein. End 384 includes a portion 396 having a height h2, as shown in FIG. 16. Portion 396 is disposable between spinal rod 150 and crown 44 to facilitate reduction height adjustment of spinal rod 150 at a selected height, similar to that described herein. End 384 includes a circumferential band 400, similar to band 100 described herein. Band 400 includes arms 402 that are moveable relative to shim 380 to capture spinal rod 150, as described herein.

In one embodiment, as shown in FIGS. 19-26, spinal implant system 10, similar to the systems and methods described herein, includes a spinal construct 500, similar to spinal construct 200 described herein. Spinal construct 500 includes bone fastener 202 and an adaptor 516, similar to adaptor 16 described herein. Adaptor 516 is disposable with implant receiver 12 of bone fastener 202, described herein, between spinal rod 150 and crown 44 to provide intra-operative spinal rod reduction height adjustment, as described herein.

Adaptor 516 includes a shim 580, similar to shim 80 described herein. Shim 580 extends between an end 582 and an end 584. Shim 580 includes a substantially linear configuration. Shim 580 is configured to provide reduction height adjustment of spinal rod 150 relative to crown 44, similar to that described herein. As shim 580 translates relative to spinal rod 150, shim 580 fills space S between spinal rod 150 and crown 44.

Figure 21:
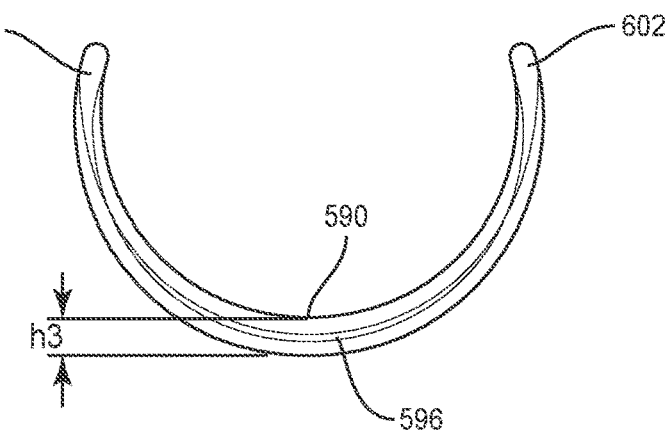
FIG. 21 is an end view of the components shown in FIG. 19.
Figure 22:
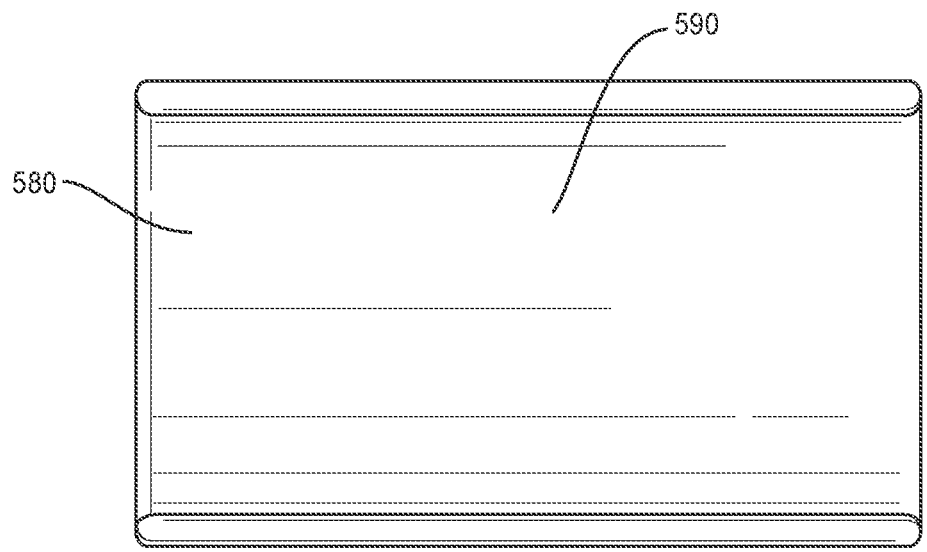
FIG. 22 is a side view of the components shown in FIG. 19.
Figure 23:
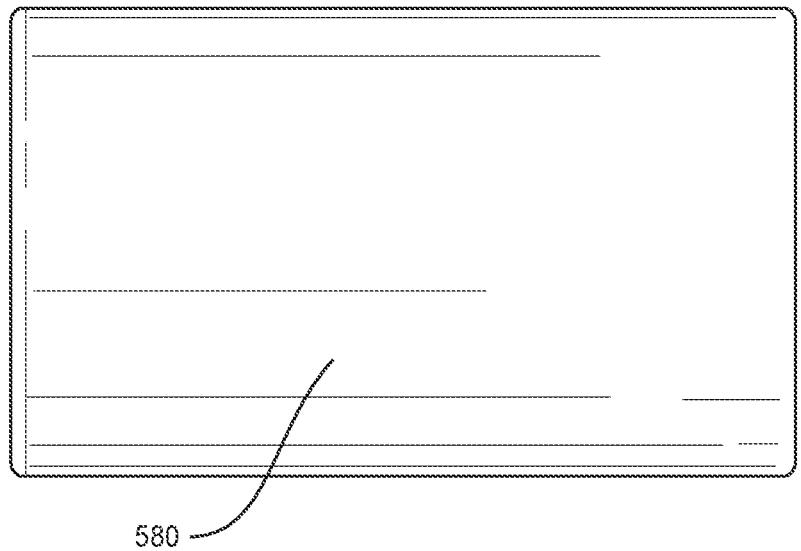
FIG. 23 is a side view of the components shown in FIG. 19.
Figure 24:
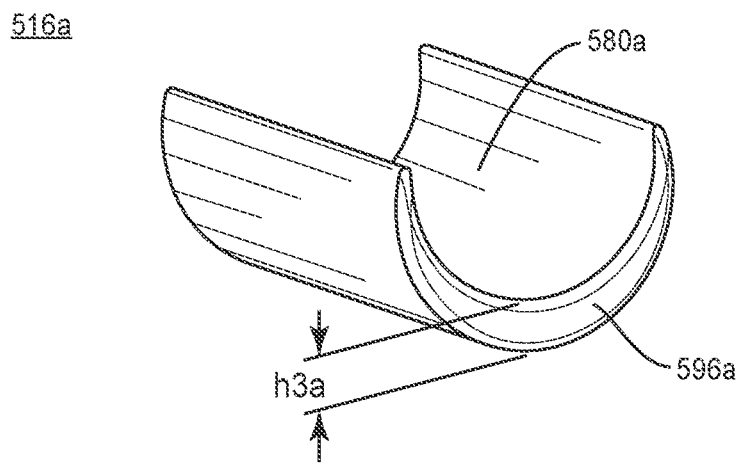
FIG. 24 is a perspective view of components of one embodiment of a spinal implant system in accordance with the principles of the present disclosure.
Figure 25:
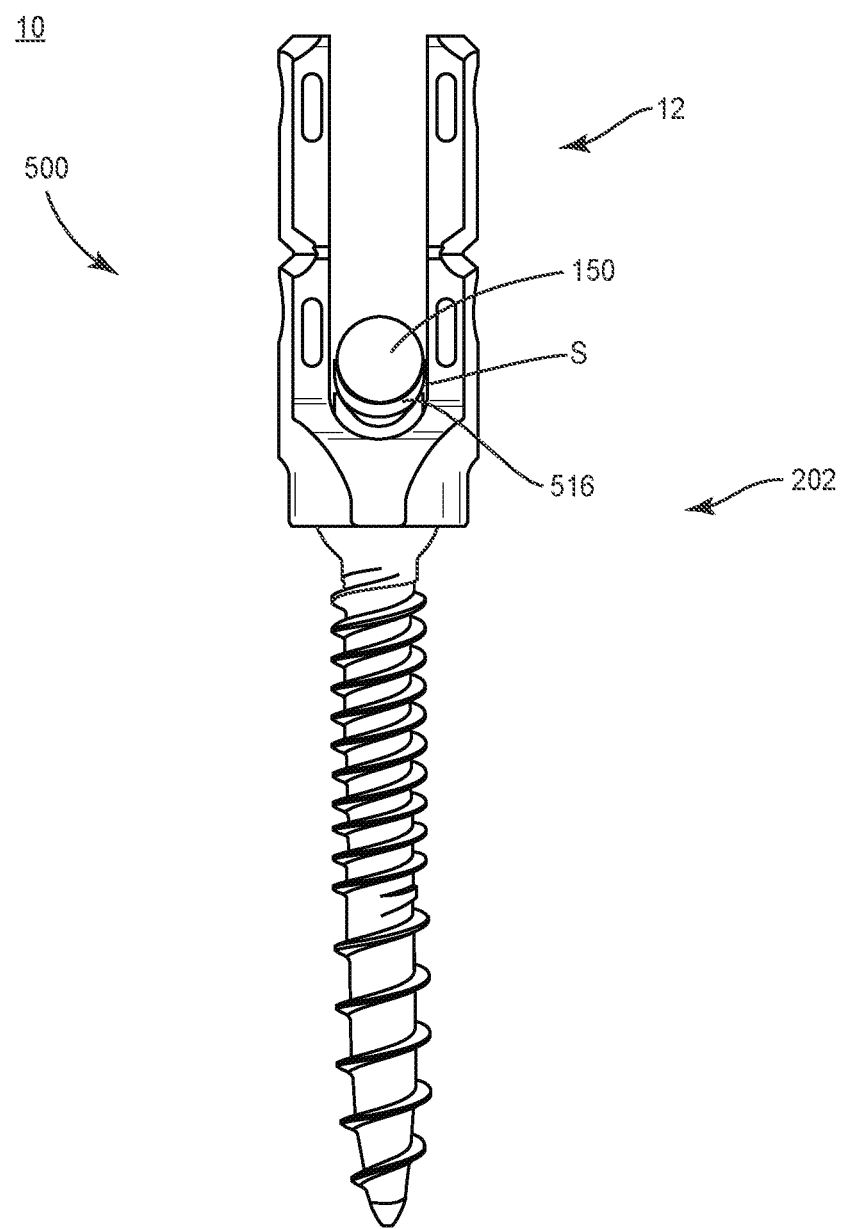
FIG. 25 is a side view of components of one embodiment of a spinal implant system in accordance with the principles of the present disclosure.
Figure 26:
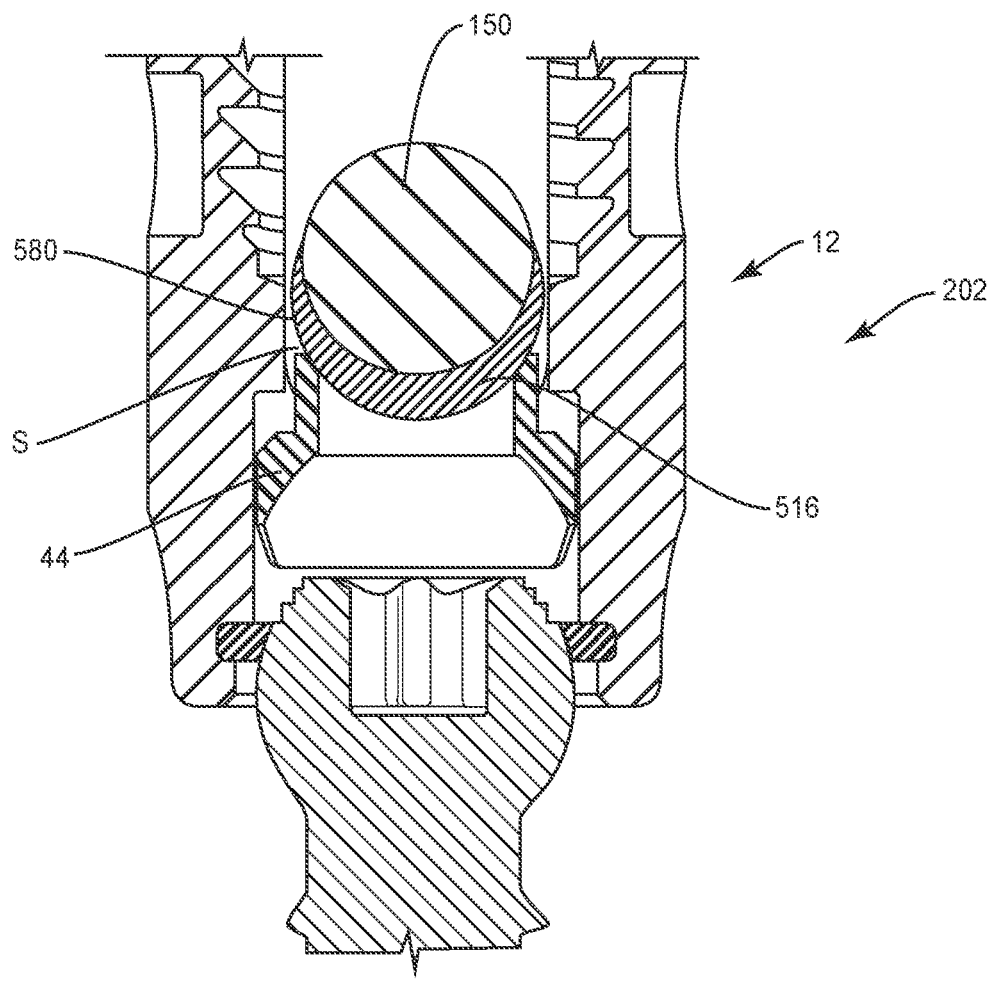
FIG. 26 is a break away cross section view of the components shown in FIG. 25.

Shim 580 includes an arcuate surface 590. Surface 590 is slidably engageable with an outer arcuate surface of spinal rod 150, as described herein. End 584 includes a portion 596 having a height h3, as shown in FIG. 21 Portion 596 is disposable between spinal rod 150 and crown 44 to facilitate reduction height adjustment of spinal rod 150, as described herein. In some embodiments, spinal implant system 10 comprises a spinal implant kit, as described herein, which includes a plurality of adaptors 516 having various sized portions 596, such as, for example, adaptor 516a including a shim 580a having a portion 596a with a height h3a, as shown in FIG. 24 and similar to the kits described herein. Shim 580 includes walls 602 that are moveable to capture spinal rod 150 in a snap fit, similar to the bands described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct adaptor comprising:
   a member being positionable between an inner surface of a bone fastener that defines an implant cavity and a spinal rod disposed with the implant cavity, the member comprising a shim having a first end having a tip comprising a bevel end surface and a second end, the first end and the second end defining a longitudinal surface configured for disposing the spinal rod; and
   a capture element connected with the member at or about the second end and engageable with the spinal rod, wherein the longitudinal surface of the shim is transverse to the capture element.

2. A spinal construct adaptor as recited in claim 1, wherein the capture element is intra-operatively engageable with the spinal rod.

3. A spinal construct adaptor as recited in claim 1, wherein the member is positioned between the spinal rod and the inner surface to selectively dispose the spinal rod relative to the inner surface.

4. A spinal construct adaptor as recited in claim 1, wherein the member is positioned between the spinal rod and a crown of the inner surface to selectively dispose the spinal rod relative to the crown.

5. A spinal construct adaptor as recited in claim 1, wherein the member is positioned between the spinal rod and the inner surface to selectively adjust a dorsal height of the spinal rod relative to tissue connected with the bone fastener.

6. A spinal construct adaptor as recited in claim 1, wherein the member includes an outer surface that is slidably engageable with an outer surface of the spinal rod.

7. A spinal construct adaptor as recited in claim 1, wherein the member includes an arcuate surface that is engageable with an outer arcuate surface of the spinal rod.

8. A spinal construct adaptor as recited in claim 1, wherein the member includes a linear tip or a tapered tip.

9. A spinal construct adaptor as recited in claim 1, wherein the capture element comprises a circumferential band disposable about at least a portion of the spinal rod.

10. A spinal construct adaptor as recited in claim 1, wherein the capture element comprises an expandable ring.

11. A spinal construct adaptor as recited in claim 1, wherein the capture element comprises movable arms extending from the member.

12. A spinal construct adaptor as recited in claim 1, wherein the capture element is engageable with the spinal rod in a snap-fit assembly.

13. A spinal construct adaptor as recited in claim 1, wherein the capture element is engageable with the spinal rod and translatable relative thereto.

14. A spinal construct adaptor as recited in claim 1, wherein the bone fastener includes an arm having a break away tab.

15. A spinal construct adaptor as recited in claim 14, wherein the break away tab is configured to fracture when 2 Nm to 8 Nm of force is applied to the break away tab.

16. A method of treating a spine, the method comprising the steps of:
reducing a spinal rod with an implant cavity of a bone fastener, the bone fastener including an inner surface defining the implant cavity;
connecting an adaptor to the spinal rod, the adaptor comprising a shim having a first end having a tip comprising a bevel end surface and a second end having a circumferential band including arms configured to capture the spinal rod, the first end and the second end defining a longitudinal axis extending along the spinal rod; and
positioning the adaptor between the inner surface and the spinal rod to selectively dispose the spinal rod relative to the inner surface to facilitate reduction of the spinal rod with the implant cavity.

17. A method as recited in claim 16, wherein the step of disposing the adaptor between the inner surface and the spinal rod includes selectively adjusting a distance of the spinal rod relative to the inner surface.

18. A method as recited in claim 16, wherein the step of connecting includes an expandable snap ring of the adaptor being engageable with the spinal rod.

19. A method as recited in claim 16, further comprising the step of translating the adaptor along the spinal rod for disposal between the inner surface and the spinal rod.

20. A spinal implant system comprising:
a bone fastener including an implant receiver having a crown;
a spinal rod disposable within the implant receiver; and
an adaptor transverse to the implant receiver being positionable between the crown and the spinal rod to selectively dispose the spinal rod relative to the crown, the adaptor comprising a shim having a first end having a tip comprising a bevel end surface and a second end comprising arms, wherein the adaptor comprises a surface between the first end and the second end, the surface configured to allow the adaptor to translate and/or rotate the spinal rod.

* * * * *